United States Patent [19]
Adams et al.

[11] Patent Number: 5,954,688
[45] Date of Patent: Sep. 21, 1999

[54] EVERTING TOROID DEVICE FOR DELIVERING A DRUG INTO A BODY CAVITY

[75] Inventors: Michael A. Adams; Jeremy P. W. Heaton, both of Kingston; James D. Banting, Oakville, all of Canada

[73] Assignee: Queen's University at Kingston, Kingston, Canada

[21] Appl. No.: 08/917,566

[22] Filed: Aug. 26, 1997

[51] Int. Cl.⁶ .................................................. A61M 31/00
[52] U.S. Cl. ................ 604/59; 604/57; 604/48; 604/311; 604/514; 604/218
[58] Field of Search ................... 604/57, 59, 60, 604/63, 271, 54, 55, 48, 53, 49, 73, 104, 105, 106, 107, 205, 309, 311, 218, 187, 181, 500, 514; 222/92, 206, 499, 501, 505, 527

[56] References Cited

U.S. PATENT DOCUMENTS

| | | |
|---|---|---|
| 268,805 | 12/1882 | Sakai et al. . |
| 602,010 | 4/1898 | Hoenig . |
| 634,982 | 10/1899 | Johnson . |
| 643,867 | 2/1900 | Vilbiss . |
| 683,589 | 10/1901 | Barry . |
| 719,586 | 2/1903 | Hasbrouck . |
| 742,634 | 10/1903 | Hall . |
| 1,628,843 | 5/1927 | Horton . |
| 1,642,950 | 9/1927 | Haas . |
| 1,685,280 | 9/1928 | Findley . |
| 3,168,092 | 2/1965 | Silverman . |
| 3,500,819 | 3/1970 | Silverman . |
| 3,589,356 | 6/1971 | Silverman . |
| 4,254,774 | 3/1981 | Boretos . |
| 4,776,848 | 10/1988 | Solazzo . |
| 4,801,444 | 1/1989 | Kravchenko . |
| 4,801,587 | 1/1989 | Voss . |
| 4,994,066 | 2/1991 | Voss . |
| 5,045,070 | 9/1991 | Rodecki et al. . |
| 5,100,383 | 3/1992 | Lichtenstein . |
| 5,171,305 | 12/1992 | Schickling et al. . |
| 5,190,192 | 3/1993 | Lina et al. . |
| 5,234,135 | 8/1993 | LaFosse et al. . |
| 5,328,099 | 7/1994 | Petit et al. . |
| 5,330,446 | 7/1994 | Weldon et al. . |
| 5,337,923 | 8/1994 | Lugez et al. . |
| 5,368,016 | 11/1994 | Henry . |
| 5,374,247 | 12/1994 | Lowery et al. . |
| 5,453,445 | 9/1995 | Henry et al. . |
| 5,474,535 | 12/1995 | Place et al. . |
| 5,482,039 | 1/1996 | Place . |
| 5,489,435 | 2/1996 | Ratcliff . |
| 5,511,698 | 4/1996 | Solignac . |
| 5,534,242 | 7/1996 | Henry et al. . |
| 5,589,156 | 12/1996 | Henry et al. . |
| 5,593,661 | 1/1997 | Henry . |

FOREIGN PATENT DOCUMENTS

| | | |
|---|---|---|
| 0 357 581 A1 | 3/1990 | European Pat. Off. . |
| 0 432 199 B1 | 7/1993 | European Pat. Off. . |
| 33 29 176 C1 | 11/1984 | Germany . |
| 88/01924 | 3/1988 | WIPO . |

OTHER PUBLICATIONS

A sample of an everting toroid toy commercially available in North America and Bermuda, purchased Sep., 1997.

*Primary Examiner*—Ronald Stright
*Assistant Examiner*—Kent Gring
*Attorney, Agent, or Firm*—Richard J. Hicks; Stephen J. Scribner; Carol Miernicki Steeg

[57] ABSTRACT

An everting toroid for use in delivering a powdered or liquid or aerosolized drug to an internal body cavity, such as the urethra, is described. The drug may be distributed on the surface of the everting toroid or may be injected through the lumen thereof via an aerosol wand which is designed to release the drug as the toroid and/or wand are withdrawn from the body cavity.

11 Claims, 4 Drawing Sheets

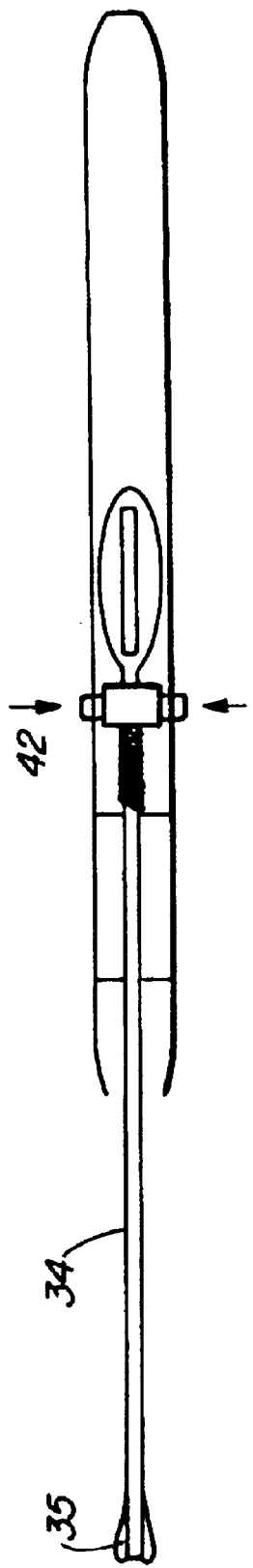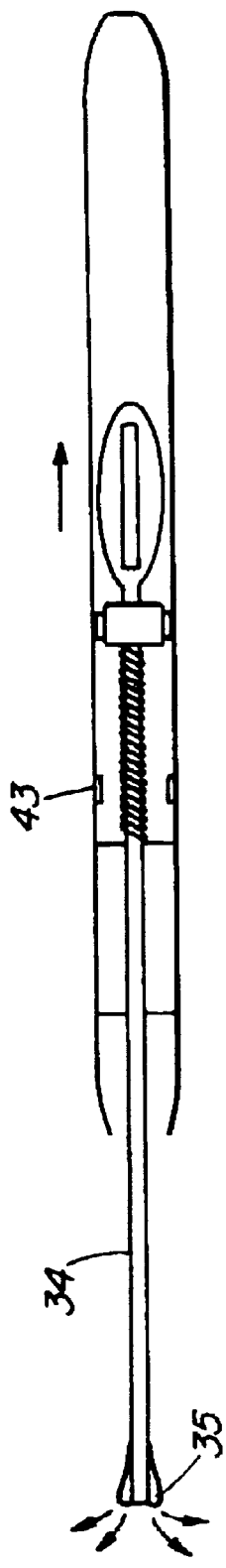

EVERTING TOROID DEVICE FOR DELIVERING A DRUG INTO A BODY CAVITY

FIELD OF INVENTION

This invention relates to an everting device for delivering a drug or other pharmaceutical preparation in powder or aerosol form to an internal body cavity. More particularly this invention relates to an everting toroid device and methods for delivering a drug or the like to the urethral lumen or other internal mucosal or absorptive surface.

BACKGROUND OF INVENTION

Everting sleeve devices for probing internal body cavities, for delivering drugs in powder form to the surfaces of those cavities and for taking samples from within the cavity are well known in the medical arts. Attention is directed to U.S. Pat. Nos. 3,168,092 issued Feb. 2, 1965, No. 3,500,819 issued Mar. 17, 1970 and No. 3,589,356 issued Jun. 29, 1971, all to Daniel Silverman, which are typical of the prior art everting sleeve devices. Essentially, a cylindrical external casing is provided with a long thin walled plastic tubing which is anchored at one end thereof to the inside wall of the casing and extends along the inside of the casing. The tubing may be open- or closed-ended. By application of external gas pressure between the casing and the tubing, the tubing is forced to turn on itself, or evert, and extend outwardly beyond the end of the casing. Powdered drugs may be applied to the everting surfaces before use and these will be deposited on the mucosa or walls of the body cavity as the tubing extends. If an open-ended tubing is employed, samples of body fluids or the like may be withdrawn through the extended tubing. Withdrawal of the tubing may be effected by withdrawing the tubing in its extended condition or by re-everting the tubing by pulling on an internally mounted withdrawal cord or the like. These prior art devices, while relatively effective, suffer from several serious disadvantages. Firstly, considerable pressure is required to evert the tubing and in the event that the tubing should fail during eversion considerable damage to sensitive and delicate body tissues may result. Secondly, withdrawing an extended tubing from a body cavity may cause considerable friction and hence discomfort or pain to the patient. Everting the extended tubing by means of an internal withdrawal cord or the like is cumbersome and not very practical in the case of very thin long tubes. There is a need, therefore, for an improved everting sleeve-type device for delivering powdered drugs and the like to long narrow body passages, such as, but not limited to, the urethra, bladder, vagina, anus, rectum and colon.

OBJECT OF THE INVENTION

An object of the present invention is to provide an improved everting toroidal low-pressure sleeve type device for delivering drugs and the like to internal body cavities. Another object of this invention is to provide an everting toroidal sleeve-type device in combination with an aerosol delivery device for delivery of drugs and the like to internal body cavities.

Yet another object is to provide novel methods for delivery of pharmaceutical compositions, such as drugs, to internal body cavities.

BRIEF STATEMENT OF INVENTION

By one aspect of this invention there is provided an apparatus for delivering a pharmaceutical composition in fluid or solid form to the lumen of an internal body cavity, comprising: a tubular housing member having a first open end and a second end; an elongated flexible toroidal member contained within said housing member and having an outer surface portion thereof secured to said housing adjacent said first open end thereof; and means adjacent said second end, contacting a surface portion of said toroidal member, and adapted to move through said housing member towards said first open end thereof so as to cause said toroidal member to evert and extend outwardly from said first open end of said housing member.

By another aspect of this invention there is provided an apparatus for delivering a pharmaceutical composition in fluid or solid form to the lumen of an internal body cavity, in combination a tubular housing member having a first open end and a second end; an elongated flexible toroidal member contained within said housing member and having an outer surface portion thereof secured to said housing adjacent said first open end thereof; means adjacent said second end, secured to an inner surface portion of said toroidal member, and adapted to move through said housing member towards said first open end thereof so as to cause said toroidal member to evert and extend outwardly from said first open end of said housing member; a second tubular housing member having a proximal end and an open distal end; tubular means contained within said second tubular housing having an open distal end and an aerosolized pharmaceutical delivery chamber at a proximal end thereof; means to extend said tubular means longitudinally outwardly from said open distal end of said second tubular housing and to retract said extended tubular means back into said second tubular housing; and valve means adjacent said delivery chamber to dispense an aerosolized pharmaceutical contained in said delivery chamber through said tubular means to said distal end thereof when said tubular means is extended from said second housing member and is retracting thereinto; wherein said tubular housing member and said toroidal member are adapted to axially receive said tubular member when in said extended position from said second tubular housing member.

By yet another aspect of this invention there is provided an apparatus wherein said means to extend said tubular means includes slide means adapted to cooperate with said second tubular housing member to extend said tubular means longitudinally therefrom.

In an alternative aspect of this invention, there is provided a method for delivering a pharmaceutical composition or mixture thereof to the lumen of an internal body cavity, comprising: providing a tubular housing member having a first open end and a second end; an elongated flexible toroidal member contained within said housing member and having an outer surface portion thereof secured to said housing adjacent said first open end; and means adjacent said second end, contacting a surface portion of said toroidal member, and adapted to move through said housing member towards said first open end thereof; adhering a selected said pharmaceutical composition to an inner surface of said toroidal member; and advancing said means adjacent said second end through said housing member so as to cause said toroidal member to evert into said internal body cavity and thereby deposit said pharmaceutical composition therein.

The body cavity may be the urethra, bladder, vagina, anus, rectum, colon, pharynx, or other suitable cavity of a subject in need of drug delivery thereto. Preferably, the body cavity is the urethra, and more preferably, the adult male urethra.

BRIEF DESCRIPTION OF DRAWINGS

FIG. 7 is a top plan view of the device of FIG. 5, shown in extended position; and FIG. 8 is a top plan view of the device of FIG. 7 shown during the withdrawal and drug delivery phase of the cycle.

DETAILED DESCRIPTION OF PREFERRED EMBODIMENTS

Figure 1:
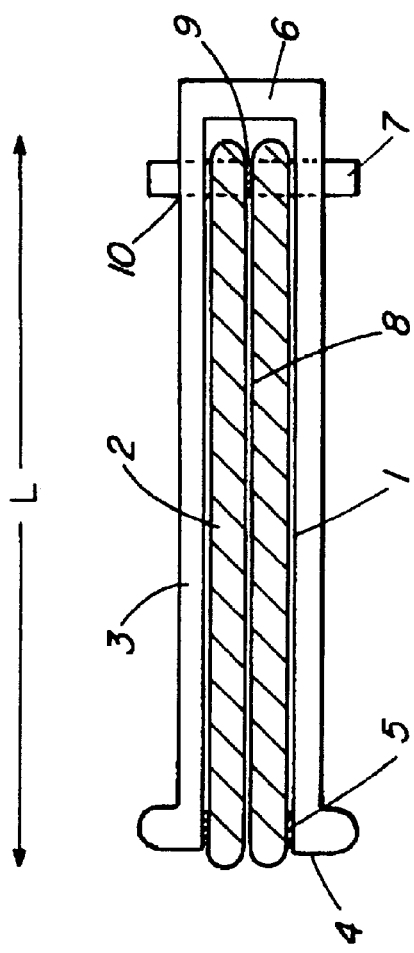
FIG. 1 is a top plan view of a drug delivery device according to one embodiment of this invention, in closed position.
Figure 3:
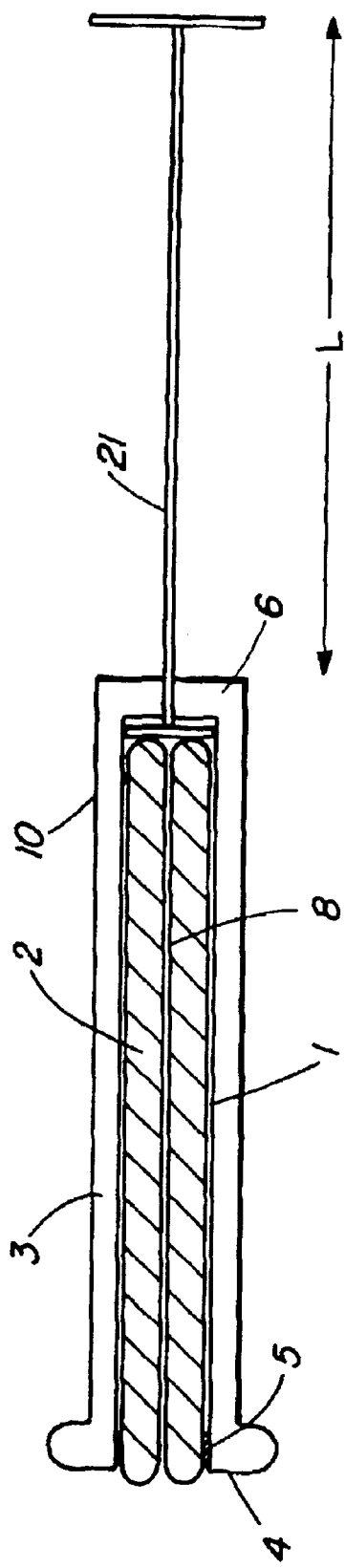
FIG. 3 is a top plan view of an alternative embodiment of the invention, in closed position.
Figure 4:
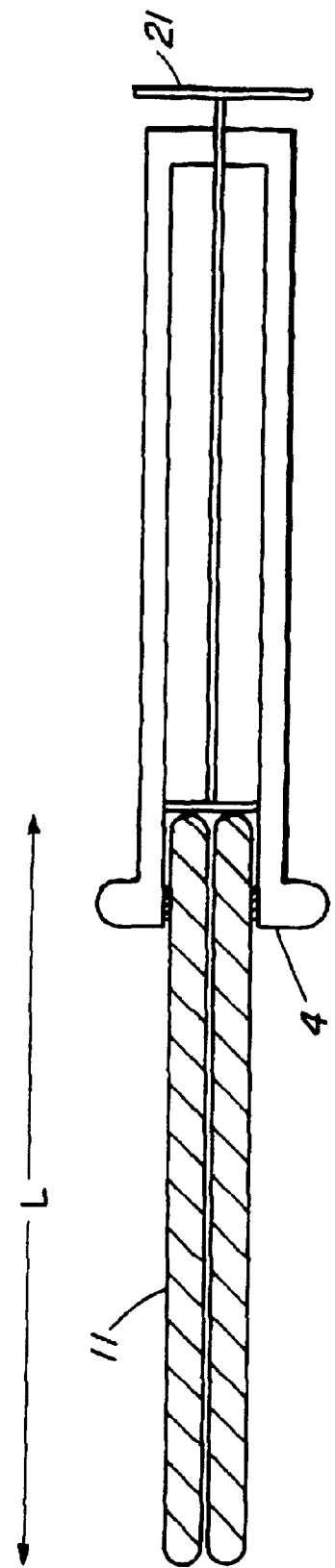
FIG. 4 is a top plan view of the device of FIG. 3 shown in extended position.

In FIG. 1 there is shown a flexible ring or toroid 1 made from a thin, physiologically inert and acceptable thermoplastic film material, such as silicone or polyurethane about 0.5 to about 50 μm thick, which is filled with a physiologically inert material 2, such as an isotonic saline solution, a gas such as nitrogen or a gel, under relatively low pressure. In some applications, such as, for example, delivery to the anus or rectum, the film may be thicker in comparison to applications such as delivery to the urethra, where the film is preferably about 0.5 to about 10 μm. Toroid 1 is elongated in one dimension so that it has a length which typically is about 5 to about 40 times the external diameter, but is not limited thereto. Depending on the specific cavity, the diameter D is preferable about 2 to about 20 mm. For example, for delivery of vasodilating drugs to the male or female urethra, the toroid will preferably have an outside diameter in the range of about 6 to about 8 mm, which is the diameter of the adult urethra, and be up to about 30 cm long so that it can be extended beyond the external part of the urethra, or fossa naviculari (in the male) which is composed of squamous epithelium cells and less absorptive, so as to reach the proximal urethra and, in some applications, the bladder. Toroid 1 is mounted inside an applicator tube 3 and secured at the open end 4 thereof by means of an adhesive 5 or the like around the surface of toroid 1. At the other, preferably closed, end 6 of the tube 3, a slide 7 is secured to the inner diameter or internal lumen 8 of toroid 1 by adhesive 9. Slide 7 moves along a slot 10 in tube 3 a distance L. In use, the physician, health professional and/or patient, places the tube 3 with the end 4 adjacent the distal urethra and slides the slide 7 towards the end 4, thereby causing the toroid to advance in a rolling action into the unopened urethra a distance L/2. The tube wall that everts from the central lumen 8 to the outside will remain stationary relative to both tube 3 and the wall of the urethra once it is in place. This means that the urethra is opened by lateral pressure only without sliding relative to the mucosa of the urethra, thereby considerably reducing any discomfort to the patient. In an alternative embodiment shown in FIGS. 3 and 4, an external plunger 21 rests against the toroid 2 but is not secured thereto. The plunger may be L to 2L in length. As the plunger is pushed in a distance L, the toroid everts a distance L as well. It will be appreciated that the internal lumen 8 of the toroid can be coated before insertion into the urethra with any selected drug or other medicament, preferably in powder form with or without a carrier therefor, so that, as the toroid everts into the urethra, the drug is deposited directly onto the urethral mucosa for direct absorption thereinto. The drug may be a salt, or even a base compound, or may be coated on the device as separate components. In some embodiments, such components may be relatively unstable in combination and mix on contact with the urethral mucosa. Alternatively, an aerosol device described in more detail hereinbelow may be inserted through the extended toroid to deliver drugs to the proximal end of the uretha and to the urethral mucosa as the device is withdrawn. Withdrawal of the toroid 1 is simply effected by the user moving slide 7 from end 4 towards closed end 6 of tube 3, thereby causing toroid 1 to invert back to the original position as shown in FIG. 1. Again, it is to be noted that there is no sliding motion between the toroid 1 and the urethral mucosa, therefore reducing friction to a minimum with increased patient comfort, and also ensuring that the deposited drug is not removed from the deposit site.

Figure 2:
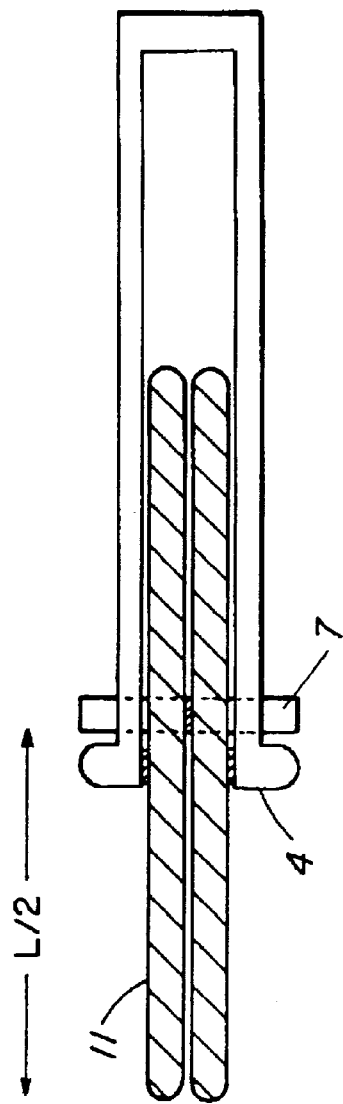
FIG. 2 is a top plan view of the device of FIG. 1 shown in extended position.
Figure 5:
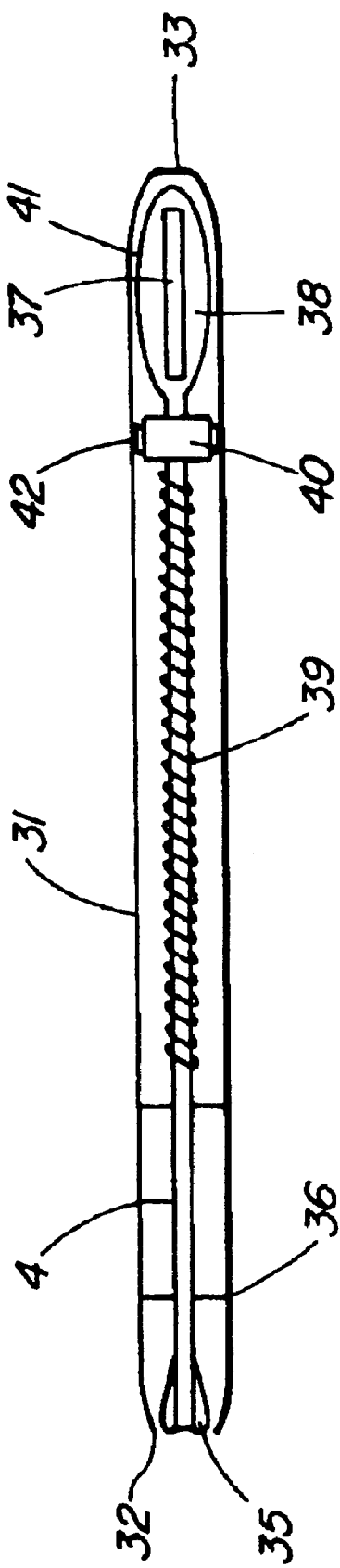
FIG. 5 is a top plan view of an aerosol drug delivery device of the present invention, in closed position.
Figure 6:
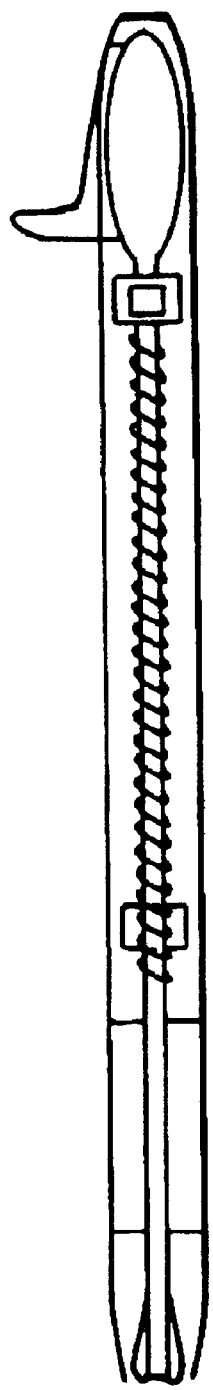
FIG. 6 is a side view of the device of FIG. 5.

Turning now to FIGS. 5–8, there is shown an aerosol device which may be directly inserted into a body cavity, such as the urethra, but preferably through or with the lumen of the everting toroid 1 of FIGS. 1 and 2. The everting toroid 1 may have already been inserted into the body cavity, or the toroid and aerosol device may be inserted into the cavity simultaneously (i.e., as a combination). As seen in FIGS. 5 and 6, an elongated tubular housing 31, having an open distal end 32 and a closed proximal end 33 is provided with an aerosol delivery tube or wand 34, preferably made from a rigid but flexible thermoplastic material, having a lubricated nylon glider 35 at the distal end 32 thereof. Glider 35 facilitates entry of the flexible aerosol delivery tube or wand 34 into the selected body cavity or into toroid 1 and eases passage centrally therethrough. Housing 31 is provided with plastic guides 36 which ensure the aerosol delivery tube 34 remains centred in housing 31. A slider 37 is provided adjacent proximal end 33 and an aerosol/gas chamber 41, containing an aerosolized drug, to facilitate sliding tube 34 out of distal end 32 of housing 31, as seen in FIG. 7. Slider 37 slides in a groove 38 in housing 31. As tube 34 advances from end 32, a spring 39 is compressed between guide 36 and aerosol release valve 40. When tube 34 is fully advanced, as seen in FIG. 7, a spring-loaded release valve button 42 is pushed radially outwardly through an appropriately located opening 43 in housing 31, as seen in FIG. 7. Upon depressing button 42, valve 40 opens and starts to release the aerosolized drug contained in chamber 41 through the tip 35 of tube 34. At the same time, button 42 is again internalized within housing 31 and is moved towards proximal end 33 thereof as compressed spring 39 extends, as seen in FIG. 8. It will be appreciated that the aerosolized drug is ejected directly onto the walls of the urethra or other body cavity as the end 35 is withdrawn, thereby painting the drug in a relatively uniform manner onto the walls, for direct assimilation without any physical contact with the withdrawing tube 34 and/or toroid 1. Preferably the drug is in the form of a base compound or salt and more preferably without a solid or liquid carrier. Solid drug may be dissolved in a non-CFC propellant such as, for example, Dymel 134A produced by DuPont, such that it becomes a gas upon expansion during delivery to the cavity. It will also be appreciated that when the aerosol device is used in combination with the toroid 1, the toroid 1 must also be withdrawn from the body cavity either together with tube 34 or in advance thereof. Preferably, tube 34 is provided with at least one longitudinally extending groove (not shown) along the outer surface thereof to allow venting of aerosol gases and prevent gas pressure build-up within the body cavity. Other venting devices will be apparent to those skilled in the art.

Similarly, alternative devices for advancing and retracting the aerosol tube based on hydraulic, electronic or mechanical principles will be apparent to those skilled in the art. For example, a gear drive and stepper motor housed in a casing could easily be used. A simple piston device is also contemplated.

We claim:

1. An apparatus for delivering a pharmaceutical composition in fluid or solid form to the lumen of an internal body cavity, comprising: a tubular housing member having a first open end and a second end; an elongated flexible toroidal member contained within said housing member and having an outer surface portion thereof secured to said housing adjacent said first open end; and means adjacent said second end, contacting a surface portion of said toroidal member, and adapted to move through said housing member towards said first open end thereof so as to cause said toroidal member to evert and extend outwardly from said first open end of said housing member.

2. An apparatus as claimed in claim 1 wherein said means adjacent said second end comprises slide means adapted to slide along said housing member.

3. An apparatus as claimed in claim 2 wherein said slide means is secured to an inner surface portion of said toroidal member.

4. An apparatus as claimed in claim 1 wherein said second end of said housing member is a closed end.

5. An apparatus as claimed in claim 1 wherein said toroidal member comprises a thin thermoplastic film member.

6. An apparatus as claimed in claim 5 wherein said film member forms a sealed envelope containing a physiologically inert fluid.

7. An apparatus as claimed in claim 6 wherein said inert fluid is selected from the group consisting of isotonic saline solution, a gas and a gel.

8. An apparatus as claimed in claim 7 wherein said toroidal member has a diameter D and a length in the range between 5 and 40 D.

9. An apparatus as claimed in claim 8 wherein said pharmaceutical composition comprises a base or salt pharmaceutical composition in powder form adhered to a surface of said toroidal member.

10. An apparatus as claimed in claim 1 wherein said means adjacent said second end comprises plunger means adjacent said toroidal member.

11. A method for delivering a pharmaceutical composition or mixture thereof to the lumen of an internal body cavity, comprising: providing a tubular housing member having a first open end and a second end; an elongated flexible toroidal member contained within said housing member and having an outer surface portion thereof secured to said housing adjacent said first open end; and means adjacent said second end, contacting a surface portion of said toroidal member, and adapted to move through said housing member towards said first open end thereof; adhering a selected said pharmaceutical composition to an inner surface of said toroidal member; and advancing said means adjacent said second end through said housing member so as to cause said toroidal member to evert into said internal body cavity and thereby deposit said pharmaceutical composition therein.

* * * * *